(12) United States Patent
DiDomenico et al.

(10) Patent No.: US 6,437,075 B1
(45) Date of Patent: *Aug. 20, 2002

(54) POLYURETHANE AND POLYUREA BIOMATERIALS FOR USE IN MEDICAL DEVICES

(75) Inventors: Edward DiDomenico, Anoka; David L. Miller, Circle Pines; Michael Eric Benz, Ramsey, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/593,255

(22) Filed: Jun. 13, 2000

Related U.S. Application Data

(62) Division of application No. 08/846,337, filed on Apr. 30, 1997, now Pat. No. 6,111,052.

(51) Int. Cl.⁷ .............................................. C08G 18/52
(52) U.S. Cl. ........................ 528/72; 528/85; 600/372; 607/119
(58) Field of Search ............................... 607/122, 119; 600/372, 373; 528/72, 85

(56) References Cited

U.S. PATENT DOCUMENTS

| | | | |
|---|---|---|---|
| 4,098,773 A | 7/1978 | Illers et al. ................. 425/65 |
| 4,191,818 A | 3/1980 | Illers et al. ................. 528/44 |
| 4,254,229 A | 3/1981 | Schwindt et al. .......... 521/163 |
| 4,285,073 A | 8/1981 | Szycher ....................... 528/79 |
| 4,289,854 A | 9/1981 | Tolbert ........................ 435/41 |
| 4,289,856 A | 9/1981 | Yamamoto et al. ........... 521/51 |
| 4,349,656 A | 9/1982 | Arendt et al. ................. 528/63 |
| 4,430,471 A | 2/1984 | Toothill et al. ............. 524/356 |
| 4,521,582 A | 6/1985 | Goyert et al. ................. 528/67 |
| 4,596,836 A | 6/1986 | Kimball et al. ............. 521/114 |
| 4,780,522 A | 10/1988 | Kajimoto et al. ............. 528/76 |
| 4,851,009 A | 7/1989 | Pinchuk ....................... 623/66 |
| 4,873,308 A | 10/1989 | Coury et al. ................. 528/75 |
| 5,001,210 A | 3/1991 | Coury et al. ................. 528/85 |
| 5,040,544 A | 8/1991 | Lessar et al. ............... 128/784 |
| 5,077,321 A | 12/1991 | Michaelis ................... 521/117 |
| 5,109,077 A | 4/1992 | Wick ........................... 525/467 |
| 5,130,198 A | 7/1992 | Swisher et al. ............. 428/391 |
| 5,133,742 A | 7/1992 | Pinchuk ......................... 623/1 |
| 5,238,006 A | 8/1993 | Markowitz ................... 607/143 |
| 5,247,004 A | 9/1993 | Swisher et al. ............. 524/494 |
| 5,318,572 A | 6/1994 | Helland et al. ............. 607/121 |
| 5,375,609 A | 12/1994 | Molacek et al. ............ 607/119 |
| 5,480,421 A | 1/1996 | Otten .......................... 607/122 |
| 5,711,959 A | 1/1998 | Kohler et al. ............... 424/423 |
| 6,149,678 A * | 11/2000 | DiDomenico ............... 607/122 |

FOREIGN PATENT DOCUMENTS

| | | | |
|---|---|---|---|
| DE | 29 45 855 A1 | 5/1980 | .......... C08G/18/14 |
| EP | 0 361 950 A3 | 9/1989 | .......... C08G/18/32 |
| EP | 0 381 125 A2 | 1/1990 | .......... C08K/13/02 |
| EP | 0 461 072 A2 | 5/1991 | ........... C08K/5/18 |
| EP | 0 624 61 2 A1 | 5/1993 | .......... C08G/18/62 |
| JP | 50-071918 | 11/1973 | |
| JP | 07-258599 | 3/1994 | |
| WO | WO 86/02933 | 5/1986 | .......... C08G/18/38 |

OTHER PUBLICATIONS

The Biostability of Polyurethane Leads, Ken Stokes, Modern Cardiac pacing editied by S. Serge Barold, MD Mount Kisco, NY, Futura Publishing Co., 1985.

Q. Zhao et al., "Cellular Interactions with Biomaterials"; in vivo cracking of pre–stressed lethane 2563–80A, J.Biomedical Materials Research 24 pp. –621–637, 1990.

M. Szycher et al., "High Performance Tecoflex Polyurethanes in Biomedical Applications" in Advances in Biomaterials; S.M. Lee, Ed.; Technomic: Lancaster, PA; pp. 110–118 (1987).

D.F. Williams, "Biodegradation of Medical Polymers" in Concise Encyclopedia of Medical and Dental Materials; D. Williams et al., Ed. Pergamon Press: Oxford; pp.–69–74 (1990).

Q. Zhao et al., "Foreign–body giant cells and polyurethane biostability: In vivo correlation of cell adhesion and surface cracking", J. Biomedical Materials Research, 25 pp. 177–183 (1991).

K. B. Stokes et al., "The Biostability of Various Polyether Polyrethanes Under Atress" in Advances in Biomaterials; S.M. Lee, Ed.; Technomic: Lancaster, PA; pp. 235–244 (1987).

A.J. Coury et al., "Biomedical Uses of Polyurethanes" In Advances in Urethane Science & Technology, vol. 9; K.C. Frisch et al Eds; Technomic: Lancaster, PA; pp. 130–168 (1984).

K. B. Dolezel et al., "In vivo degradation pf polymers", Biomaterial, 10 pp. 96–100 (Mar. 1989).

A.J. Courey et al. "Biostability Considerations for Implantable Polyurethanes" Life Support Systems 5, pp.–25–39 (1987).

* cited by examiner

Primary Examiner—Rachel Gorr
(74) Attorney, Agent, or Firm—Kenneth J. Collier; Girma Wolde-Michael; Thomas Woods

(57) ABSTRACT

A medical device comprising a biomaterial formed from a polymer comprising urethane groups, urea groups, or combinations thereof, and sacrificial moieties that preferentially oxidize relative to other moieties in the polymer.

5 Claims, 4 Drawing Sheets

POLYURETHANE AND POLYUREA BIOMATERIALS FOR USE IN MEDICAL DEVICES

This application is a division of application Ser. No. 08/846,337, filed Apr. 30, 1997, now U.S. Pat. No. 6,010,052.

FIELD OF THE INVENTION

This invention relates to medical devices that include polyurethane and polyurea biomaterials, particularly elastomers, containing sacrificial moieties (e.g., sulfur-containing moieties) that preferentially oxidize relative to other moieties in the polymer.

BACKGROUND OF THE INVENTION

The chemistry of polyurethanes and polyureas is extensive and well developed. Typically, polyurethanes and polyureas are made by a process in which a polyisocyanate is reacted with a molecule having at least two hydrogen atoms reactive with the polyisocyanate, such as a polyol or polyamine. The resulting polymer can be further reacted with a chain extender, such as a diol or diamine, for example. The polyol or polyamine can be a polyester, polyether, or polycarbonate polyol or polyamine, for example.

Polyurethanes and polyureas can be tailored to produce a range of products from soft and flexible to hard and rigid. They can be extruded, injection molded, compression molded, and solution spun, for example. Thus, polyurethanes and polyureas, particularly polyurethanes, are important biomedical polymers, and are used in implantable devices such as artificial hearts, cardiovascular catheters, pacemaker lead insulation, etc.

Commercially available polyurethanes used for implantable applications include BIOMER segmented polyurethanes, manufactured by Ethicon, Inc., of Sommerville, N.J., PELLETHANE segmented polyurethanes, sold by Dow Chemical. Midland, Mich., and TECOFLEX segmented polyurethanes sold by Thermedics, Inc., Woburn, Mass. These polyurethanes and others are described in the article "Biomedical Uses of Polyurethanes," by Coury et al., in *Advances in Urethane Science and Technology*, 9, 130–168, edited by Kurt C. Frisch and Daniel Klempner, Technomic Publishing Co., Lancaster, Pa. (1984). Typically, polyether polyurethanes exhibit more biostability than polyester polyurethanes, and are therefore generally preferred biopolymers.

Polyether polyurethane elastomers, such as PELLETHANE 2363-80A (P80A) and 2363-55D (P55D), which are believed to be prepared from polytetramethylene ether glycol (PTMEG) and methylene bis(diisocyanatobenzene) (MDI) extended with butane diol (BDO), are widely used for implantable cardiac pacing leads. Pacing leads are insulated wires with electrodes that carry stimuli to tissues and biologic signals back to implanted pulse generators. The use of polyether polyurethane elastomers as insulation on such leads has provided significant advantage over silicone rubber, primarily because of the higher tensile strength and elastic modulus of the polyurethanes.

There is some problem, however, with stress cracking of polyether polyurethane insulation, which can cause failure. Polyether polyurethanes are susceptible to oxidation in the body, particularly in areas that are under stress. When oxidized, polyether polyurethane elastomers lose strength and form cracks, which eventually breach the insulation. This, thereby, allows bodily fluids to enter the lead and form a short between the lead wire and the implantable pulse generator (IPG). It is believed that the ether linkages degrade, perhaps due to metal ion catalyzed oxidative attack at stress points in the material.

One approach to solving this problem has been to coat the conductive wire of the lead. Another approach has been to add an antioxidant to the polyurethane. Yet another approach has been to develop new polyurethanes that are more resistant to oxidative attack. Such polyurethanes include only segments that are resistant to metal induced oxidation, such as hydrocarbon- and carbonate-containing segments. For example, polyurethanes that are substantially free of ether and ester linkages have been developed. This includes the segmented aliphatic polyurethanes of U.S. Pat. No. 4,873,308 (Coury et al.). Although such materials produce more stable implantable devices than polyether polyurethanes, there is still a need for biostable polymers, particularly polyurethanes suitable for use as insulation on pacing leads.

SUMMARY OF THE INVENTION

The present invention relates to medical devices comprising a biomaterial formed from a polymer comprising urethane groups, urea groups, or combinations thereof (i.e., polyurethanes, polyureas, or polyurethane-ureas). Preferably, the polymer is a segmented polyurethane. The polymer also includes sacrificial moieties (preferably in the polymer backbone) that preferentially oxidize relative to all other moieties in the polymer. These sacrificial moieties are present upon initial formation of the polymer and oxidize upon contact with the environment or body, for example. Significantly, the oxidation of such sacrificial moieties typically provides improved mechanical properties, such as increased tensile strength and/or increased modulus of elasticity, relative to the polymer prior to oxidation. As used herein, "sacrificial moiety" refers to the atom(s) or functional group that has the lowest oxidation potential within the molecule. Such moieties are the preferential sites for oxidation. Preferably, the sacrificial moiety is a sulfur- or phosphorus-containing moiety, more preferably, a sulfur-containing moiety, which can be oxidized to form a functional group that imparts stronger mechanical properties to the polymer. More preferably, the polymer includes at least about 1.0 weight percent sulfur or phosphorus, and most preferably, at least about 1.2 weight percent sulfur or phosphorus (preferably, sulfur), based on the total weight of the polymer. The polymer is also preferably substantially free of ester linkages and more preferably, substantially free of ester and ether linkages.

Preferably, the biomaterials of the present invention are used in a pacing lead as the insulation. Thus, the present invention provides a medical electrical lead comprising: an elongate insulation sheath formed from a polymer comprising urethane groups, urea groups, or combinations thereof, and sacrificial moieties (preferably in the polymer backbone) that preferentially oxidize relative to all other moieties in the polymer, as described above; an elongated conductor, located within the elongated insulation sheath; an electrode coupled to a distal end of the elongated conductor; and an electrical connector coupled to a proximal end of the elongated conductor.

The present invention also provides a medical device comprising a biomaterial formed from a segmented polymer comprising urethane groups, urea groups, or combinations thereof, wherein the polymer is prepared from isocyanate-containing compounds and compounds of the formula:

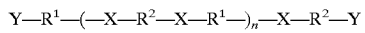

wherein Y is either OH or $NH_2$, n=0–100 (preferably 0–10), X is S or P—$R^3$, $R^1$ and $R^2$ are each independently straight, branched, or cyclic aliphatic groups (preferably alkyl groups), and $R^3$ is an aliphatic, aromatic, or araliphatic group. These sulfur and phosphorus-containing groups are the preferred sacrificial moieties that can be oxidized to functional groups that preferably provide enhanced mechanical properties to the polymer. For example, a sulfur atom or sulfide (—S—) can be oxidized to a sulfoxide or sulfoxy (—S(O)—) group (with an IR peak at about 1030 $cm^{-1}$) and then to a sulfone (—$SO_2$—) group (with an IR peak at 1125 $cm^{-1}$ upon oxidation). Sulfoxide- and sulfone-containing polymers typically have a higher tensile strength and a higher modulus of elasticity than similar polymers containing sulfide moieties.

Also provided is a medical device comprising a biomaterial formed from a polymer comprising alternating soft and hard segments linked by urethane groups, urea groups, or combinations thereof, wherein: (a) the soft segments are of the formula (—O or —OCNH)—($R^a$—U—$R^b$—U)$_y$—$R^a$—(O— or NHCO—), wherein: (i) each $R^a$ and $R^b$ is independently a hydrocarbon moiety that can include linear, branched, cyclic structures, or combinations thereof, having a molecular weight of less than about 4000, wherein at least one $R^a$ or $R^b$ noncrystallizing in the polymer at ambient temperature; (ii) each U is independently a urethane group or a urea group; and (iii) y is the average number of repeating units, which is about 1–1000; (b) the hard segments are of the formula (—O or —OCNH)—($R^c$—U—$R^d$—U)$_z$—$R^c$—(O— or NHCO—), wherein: (i) each $R^c$ and $R^d$ is independently a hydrocarbon moiety that can include linear, branched, cyclic structures, or combinations thereof, having a molecular weight of less than about 1000, wherein at least one $R^c$ or $R^d$ is crystallizing in the polymer at ambient temperature; (ii) each U is independently a urethane group or a urea group; and (iii) z is the average number of repeating units, which is about 1–1000; and (c) at least one of the soft segments or the hard segments includes a sulfur-containing or a phosphorus-containing moiety in the polymer backbone.

The present invention also provides a segmented polyurethane comprising alternating soft and hard segments linked by urethane groups, urea groups, or combinations thereof, and at least one of the soft segments or the hard segments includes a sulfur-containing or a phosphorus-containing moiety in the polymer backbone. The soft segments are of the formula (—O or —OCNH)—($R^a$—U—$R^b$—U)$_y$—$R^a$—(O— or NHCO—) wherein: each $R^a$ and $R^b$ is independently a hydrocarbon moiety that can include linear, branched, cyclic structures, or combinations thereof, having a molecular weight of less than about 4000, wherein at least one $R^a$ or $R^b$ is noncrystallizing in the polymer at ambient temperatures; each U is independently a urethane group or a urea group; and y is the average number of repeating units, which is about 1–1000. The hard segments are of the formula (—O or —OCNH)—($R^c$—U—$R^d$—U)$_z$—$R^c$—(O— or NHCO—) wherein: each $R^c$ and $R^d$ is independently a hydrocarbon moiety that can include linear, branched, cyclic structures. or combinations thereof, having a molecular weight of less than about 1000, wherein at least one $R^c$ or $R^d$ is crystallizing in the polymer at ambient temperature; each U is independently a urethane group or a urea group; and z is the average number of repeating units which is about 1–1000.

The present invention further provides a method of making a medical device comprising a biomaterial. The method includes: combining at least one isocyanate-containing compound with at least one diol- or diamine-containing compound to form the biomaterial comprising urethane groups, urea groups, or combinations thereof, and sacrificial moieties that preferentially oxidize relative to all other moieties in the polymer; and forming a medical device with the biomaterial.

The present invention also provides a method of using a medical device comprising a biomaterial. The method includes: providing a medical electrical lead comprising a biomaterial comprising urethane groups, urea groups, or combinations thereof, and sacrificial moieties that preferentially oxidize relative to all other moieties in the polymer; implanting the medical electrical lead into a vein or artery of a mammal; electrically connecting a first end of the medical electrical lead to implantable medical device; and electrically stimulating or sensing a second end of the lead.

As used herein, "ambient temperature" refers to typical room temperatures, e.g., about 17–25° C. A "crystallizing" material is one that forms ordered domains (i.e., aligned molecules in a closely packed matrix), as evidenced by Differential Scanning Calorimetry, without a mechanical force being applied. A "strain crystallizing" material is one that forms ordered domains when a strain or mechanical force is applied. A "crystalline" material is one that has an ordered packing. A "noncrystallizing" material is one that forms amorphous domains, and nonglassy domains in the polymer at ambient temperatures. A "noncrystalline" material is one that is amorphous and nonglassy. A "semicrystalline" material is one that has both amorphous domains and crystalline domains.

As used herein, a "biomaterial" may be defined as a material that is substantially insoluble in body fluids and tissues and that is designed and constructed to be placed in or onto the body or to contact fluid or tissue of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; and will substantially maintain its physical properties and function during the time that it remains implanted in or in contact with the body. A "biostable" material is one that is not broken down by the-body, whereas a "biocompatible" material is one that is not rejected by the body.

As used herein, a "medical device" may be defined as a device that has surfaces that contact blood or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like, that are implanted in blood vessels or in the heart. This can also include devices for temporary intravascular use such as catheters, guide wires, and the like which are placed into the blood vessels or the heart for purposes of monitoring or repair.

DETAILED DESCRIPTION OF THE INVENTION

Figure 1:
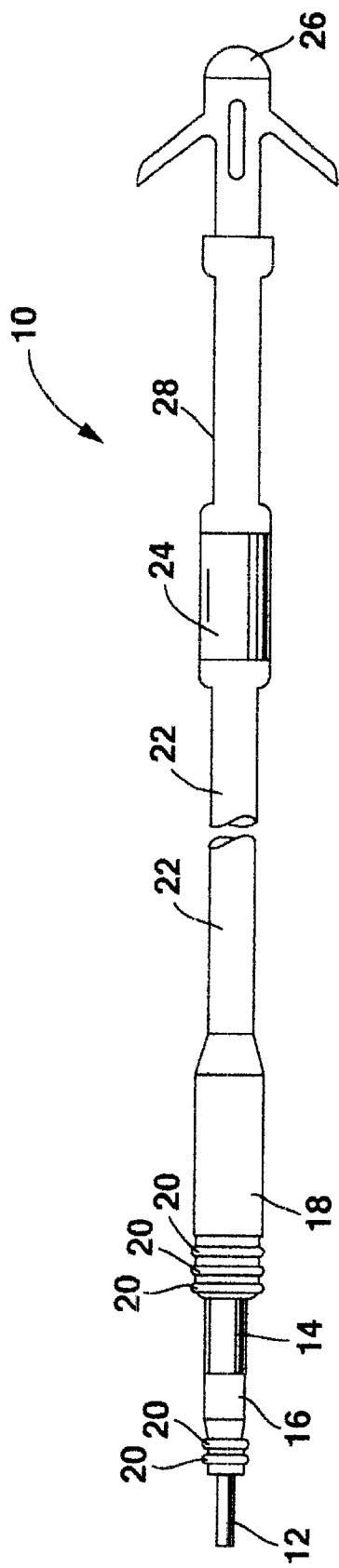
FIG. 1 is a plan view of a pacing lead according to the present invention.

The present invention provides polymers that include, upon initial formation, a sacrificial moiety susceptible to oxidation. Significantly, upon oxidation, the mechanical properties of the polymer generally improve compared to the polymer prior to oxidation. The sacrificial moiety is incorporated into the matrix of the polymer and oxidized to form a functional group that typically imparts stronger properties, particularly higher tensile strength and modulus of elasticity, for example, to the polymer. It is also believed that the oxidized moiety may provide additional hydrogen bonding interactions and crystallinity to the polymer, thereby contributing to the enhanced mechanical properties of the polymer. This improved strength occurs with time upon oxidation as a result of contact with the environment or body. Eventually, however, as with most polymers, these polymers will eventually degrade over extended periods of time in an oxidizing environment.

The polymers suitable for forming the biomaterials for use in the medical devices of the present invention are polyurethanes, polyureas, or polyurethane-ureas. These polymers can vary from hard and rigid to soft and flexible. Preferably, the polymers are elastomers. An "elastomer" is a polymer that is typically capable of being stretched to approximately twice its original length and retracting to approximately its original length upon release.

Preferably, the polymers are segmented (i.e., containing both hard and soft domains) and are comprised substantially of alternating relatively soft segments and relatively hard segments, although nonsegmented polymers are also within the scope of the present invention. Either the hard or the soft segments, or both, include a sacrificial moiety that is preferentially oxidized relative to any other moiety (i.e., atom(s) or functional group) in the polymer. As used herein, a "hard" segment is one that has a relatively higher concentration of urethane or urea groups and hence is either crystalline at ambient temperature or amorphous with a glass transition temperature above ambient temperature, and a "soft" segment is one that has a relatively low concentration of urethane or urea groups and hence is amorphous with a glass transition temperature below ambient temperature. A crystalline moiety or segment is one that adds considerable strength and higher modulus to the polymer. Similarly, a noncrystalline moiety or segment is one that adds flexibility and lower modulus, but may add strength particularly if it undergoes strain crystallization, for example. The random or alternating soft and hard segments are linked by urethane and/or urea groups and the polymers may be terminated by hydroxyl, amine, and/or isocyanate groups.

Although certain preferred polymers are described herein, the polymers used to form the biomaterials in the medical devices of the present invention can be a wide variety of polymers comprising urethane groups, urea groups, or combinations thereof. Examples of such polymers are described in U.S. Pat. No. 4,191,818 (Illers et al.), U.S. Pat. No. 4,521,582 (Goyert et al.), and U.S. Pat. No. 4,098,773 (Illers et al.). Such polymers are prepared from isocyanate-containing compounds, such as polyisocyanates (preferably diisocyanates) and compounds having at least two hydrogen atoms reactive with the isocyanate groups, such as polyols and/or polyamines (preferably diols and/or diamines). Any of these reactants can include a sacrificial moiety (preferably in the polymer backbone) that is preferentially oxidized as described herein, although preferably the sacrificial moiety is provided by the polyols and/or polyamines, particularly diols and/or diamines (including the diols or diamines of the dimer acid described below). The sacrificial moiety is preferably nonionic, and also preferably in the polymer backbone.

The sacrificial moiety can be a sulfur-containing moiety, such as monosulfides and polythioethers. It can also be a phosphorus-containing moiety, such as isobutyl bis-hydroxypropyl phosphine. The presence of the sacrificial moiety, preferably the sulfur- or phosphorus-containing moiety, and more preferably the sulfur-containing moiety, provides a polymer that is more resistant to oxidative degradation than the corresponding polymer that does not contain the sacrificial moiety. This polymer is capable of improved strength properties (e.g., tensile strength, modulus of elasticity, etc.) upon oxidation, particularly because these moieties are bound into the polymer matrix, and also because they provide increased hydrogen bonding capability upon oxidation.

Preferably, the polymer includes at least about 1.0 weight percent of the oxidizable atom (e.g., sulfur or phosphorus) of the sacrificial moiety, based on the total weight of the polymer. More preferably, the polymer includes at least about 1.2 weight percent of the oxidizable atom, and even more preferably, at least about 1.4 weight percent of the oxidizable atom. Most preferably, the polymer includes at least about 2.0 weight percent of the oxidizable atom. Preferably, the oxidizable atom of the sacrificial moiety is sulfur.

The presence of the sacrificial moieties provides an improvement in mechanical properties over time when the polymer is in an oxidizing atmosphere. Preferably, there is an increase of at least about 25% in the modulus of elasticity, and more preferably, at least about 50%, upon oxidation of the polymer when compared to the polymer prior to oxidation. Eventually, however, upon even further oxidation, the mechanical properties of the polymer can decrease as a result of polymer degradation, as do similar polymers without the sacrificial moiety. It will be understood by one skilled in the art that the mechanical properties of many polymers can increase slightly upon initial oxidation, however, this is believed to occur as a result of crosslinking, which is typically the first step in degradation.

Preferably, both the hard and soft segments are themselves substantially ether- and ester-free polyurethanes, polyureas, or combinations thereof. Herein, a substantially ether-free polymer or segment thereof is substantially free of R—O—R linkages (i.e., ether linkages containing an oxygen), and a substantially ester-free polymer or segment thereof is substantially free of R(O)—O—R linkages (i.e., ester linkages containing only oxygen). This does not include thioethers (i.e., R—S—R linkages), for example.

A preferred source of a sacrificial sulfur- or phosphorus-containing moiety is a compound of the formula (Formula I):

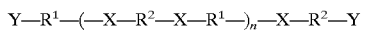

wherein Y is either OH or $NH_2$, n=0–100 (preferably 0–10), X is S or P—$R^3$, $R^1$ and $R^2$ are each independently straight, branched, or cyclic aliphatic groups (preferably having 2–22 carbon atoms, more preferably 2–11 carbon atoms, and most preferably 2–8 carbon atoms), and $R^3$ is an aliphatic (including cycloaliphatic), aromatic, or araliphatic group (i.e., a combination of aliphatic and aromatic groups, including aralkyls and alkaryls). Preferably, $R^1$ and $R^2$ groups are alkyls. Examples of suitable materials include thiodiethanol, 3,3'-thiodipropanol, 4,4'-thiodibutanol, 1,4-dithane-2,5-diol, 3-ethylthio-1,2-propanediol, polytetramethylenethioether diol, isobutylhydroxypropylphosphine, 2,2'-thiodiethylamine, 3,6-dithia-1,8-octanediol, isobutylhydroxymethylphosphine, isobutylaminopropylphosphine, phenylhydroxypropylphosphine, etc. (available from Aldrich Chemical Co., Inc., Milwaukee, Wis., and Cytec, West Paterson, N.J., for example).

It should be understood, however, that diols or diamines that do not contain sulfur- or phosphorus-containing moieties can also be used, as long as the resultant polyurethane includes at least some sulfur- and/or phosphorus-containing moieties either from diols or diamines or other reactants. Also, other polyols and/or polyamines can be used, including polyester and polyether polyols, for example, although polyester polyols are less preferred because they produce less biostable materials. Furthermore, the polyols and polyamines can be aliphatic (straight, branched, or cyclic aliphatic), araliphatic, and aromatic (including heterocyclic). Examples of suitable materials include 1,10-decane diol, 1,12-dodecane diol 9-hydroxymethyl octadecanol, cyclohexane-1,4-diol, cyclohexane-1,4-bis (methanol), cyclohexane-1,2-bis(methanol), ethylene glycol, propylene glycol, trimethylene glycol, 1,2-butylene glycol, 1,3-butane diol, 1,4-butane diol, 1,5-pentane diol, 1,2-hexylene glycol, 1,2-cyclohexane diol, 2-butene-1,4-diol, 1,6-hexane diol, diol derivative of dimer acid (DIMEROL), and so forth.

Suitable isocyanate-containing compounds for preparation of polyurethanes, polyureas, or mixtures thereof, are typically aliphatic, cycloaliphatic, araliphatic, aromatic, and heterocyclic polyisocyanates. In addition to the isocyanate groups they can include other functional groups such as biuret, urea, siloxane, etc., that are typically used in biomaterials. Suitable examples of polyisocyanates include 4,4'-diisocyanatodiphenyl methane (MDI), 4,4'-diisocyanatodicyclohexyl methane (HMDI), cyclohexane-1,4-diisocyanate, cyclohexane-1,2-diisocyanate, isophorone diisocyanate, hexamethylene-1,6-diisocyanate, tolylene diisocyanates, naphthylene diisocyanates, benzene-1,4-diisocyanate, xylene diisocyanates, diisocyanate derivative of dimer acid (DDI), and so forth.

In preferred segmented polymers, soft segments are preferably based upon noncrystallizing hydrocarbon backbones such as dimer acid derivatives, linked by urethane and/or urea groups to short and/or medium chain length hydrocarbon moieties. The dimer acids are described and discussed in the book *The Dimer Acids* edited by Edward C. Leonard, published by Humko Shefield Chemical (1975). Dimer acids are the reaction product of a Diels-Alder addition or other coupling reaction of two aliphatic, unsaturated fatty acids, typically having 18 carbon atoms. Dimer acids take the form of single or double ring structures or branched chain hydrocarbon structures, having a variety of structural formulas.

Preferably, the soft segments of polyurethanes according to the present invention consist of noncrystallizing hydrocarbon backbones such as dimer acid derivatives, alternating or randomly dispersed with short to medium chain hydrocarbon moieties and linked to them by urethane and/or urea groups. The soft segments may be produced by reacting either a diol and/or diamine derivative of dimer acid or a diisocyanate derivative of dimer acid with short to medium chain diols, diamines, and/or diisocyanates. Due to the commercial availability of dimer diisocyanate, it is anticipated that in most cases the first segments will be fabricated using dimer diisocyanate and short to medium chain length diols and/or diamine. However, reaction of diol and/or diamine derivatives of dimer acid with short to medium chain diisocyanates is also considered appropriate.

Dimer diisocyanate is a readily commercially available product, in which the hydrocarbon backbones of dimer acid have two of their substituent groups terminated in isocyanate groups rather than carboxylic acid groups. For purposes of the present invention, it is believed desirable to secure as pure a supply of dimer diisocyanate as is possible, with only very limited quantities of trimer, monomer, and other oligomers. The hydrocarbon backbones of dimer acid as well as trimethyl hexamethylene diisocyanate and 1,8-/1,9-heptadecane diisocyanate are believed particularly advantageous for incorporation in the relatively soft segments of a segmented polyurethane. Their variety of branched and cyclic isomers provide chemically stable hydrocarbon backbones with desirable mechanical properties.

In addition to the hydrocarbon backbones of dimer diisocyanate or other dimer acid derivatives, the soft segments of the polyurethanes of the present invention include one or more short to medium chain length hydrocarbon moieties derived from diols, diamines, and/or diisocyanates having a molecular weight of less than about 4000. Preferably, these moieties should be derived from medium chain diols, diamines, and/or diisocyanates having a molecular weight of about 146–1000.

The medium chain diols or diamines should have a chain length of at least about 8 carbon atoms (in addition to the S or P moiety) separating the hydroxyl or amine groups. Diols are generally preferred. Appropriate medium chain diols are listed above. They also include diol derivatives of dimer acid. Other diols or diamines having generally linear hydrocarbon chain lengths of 8 or more carbons separating the hydroxyl or amine groups (in addition to the S or P moiety) and having hydrocarbon side chains are believed to be similarly advantageous.

In some embodiments, it is desirable to include short chain hydrocarbon moieties in the relatively soft segment. These short hydrocarbon moieties may be derived from short chain diols, diamines, and/or diisocyanates having chain lengths of 2–6 carbons (in addition to the S or P moiety) between the hydroxyl or amine groups. Again diols are generally preferred. Appropriate short chain diols are listed above. If a diol derivative of dimer acid such as dimerol is used to provide the dimer acid backbones, short chain diisocyanates can serve as the source of these short chain hydrocarbon moieties. In some embodiments, inclusion of such short chain hydrocarbon moieties, with or without a sulfur or phosphorus moiety, appears to enhance mechanical properties without unduly reducing flexibility.

The relatively hard segments of the polymers used in the medical devices of the present invention are preferably fabricated from short to medium chain diisocyanates and short to medium chain diols or diamines, all of which preferably have molecular weights of less than about 1000. Appropriate short to medium chain diols, diamines, and diisocyanates include straight chain, branched, and cyclic aliphatics, although aromatics can also be used. Examples of diols and diamines useful in these more rigid segments include both the short and medium chain diols or diamines discussed above.

In cases where the relatively softer segments are produced by reacting low noncrystalline Tg isocyanates (i.e., having a Tg of below ambient temperature), such as dimer diisocyanate, trimethylhexamethylene diisocyanate, 1,8-/1, 9-heptadecane diisocyanate, with an excess of diols of the types described above, the softer segments will have the general formula —O—($R^3$—OOCNH—D—NHCOO)$_m$—$R^3$—O— wherein D signifies a noncrystallizing hydrocarbon moiety which can include linear, branched, cyclic structures, or combinations thereof, such as dimer acid derivative, trimethylhexamethylene, or 1,8-/1,9-heptadecane, and $R^3$ signifies a hydrocarbon moiety derived from a diol that does not raise the Tg of the segment above ambient temperature, and is preferably strain crystallizing. The "m" signifies the average number of repeating units, which is typically about 1–1000. Similarly, if an excess of a noncrystalline diol, such as dimer diol, trimethyl hexamethylene diol, 10-hydroxymethyloctadecanol is reacted with diisocyanates to produce the first, relatively softer segments, the general formula would be —O—(D—OOCNH—$R^4$—NHCOO)$_n$—D—O— wherein D signifies a noncrystallizing hydrocarbon moiety which can include linear, branched, cyclic structures, or combinations thereof, such as a dimer acid derivative, and $R^4$ signifies a hydrocarbon moiety derived from a diisocyanate that does not raise the Tg of the segment above ambient temperature and is preferably strain crystallizing. In addition to MDI, examples of such diisocyanates include toluene diisocyanate (TDI), 1,6-hexamethylene diisocyanate (HDI), HMDI (dicyclohexylmethane diisocyanate), and isophorone diisocyanate (IPDI). The "n" signifies the average number of repeating units, which is typically about 1–1000.

If the softer segments are produced by combining diols with an excess of noncrystalline isocyanates, the general formula would be —OCNH—(D—NHCOO—$R^5$—OOCNH)O—D—NHCO— wherein D signifies a noncrystallizing hydrocarbon moiety which can include linear, branched, cyclic structures, or combinations thereof, and $R^5$ signifies a hydrocarbon moiety derived from a diol that does not raise the Tg of the segment above ambient temperature and is preferably strain crystallizing. The "o" signifies the average number of repeating units, which is typically about 1–1000. Similarly, if the softer segments are produced by combining a diol derivative with an excess of diisocyanates, the general formula would be —OCNH—($R^6$—NCHOO—D—OOCNH)$_p$—$R^6$—NHCO— wherein D signifies a noncrystallizing hydrocarbon moiety which can include linear, branched, cyclic structures of a diol, or combinations thereof, and $R^6$ signifies a hydrocarbon moiety derived from a diisocyanate that does not raise the Tg of the segment above ambient temperature and is preferably strain crystallizing. The "p" signifies the average number of repeating units, which is typically about 1–1000.

If the softer segments are produced using an excess of diols, the general formula for the harder segments would be —OCNH—($R^7$—NCHOO—$R^8$—OOCNH)$_q$—$R^7$—NHCO— wherein $R^8$ signifies a moiety derived from a diol, and $R^7$ signifies a moiety derived from a diisocyanate of the types described above (e.g., MDI, TDI, HDI, HMDI, and IPDI). The "q" signifies the average number of repeating units, which is typically about 1–1000. If the softer segments were produced using an excess of diisocyanates, the general formula for the harder segments would be —O—($R^7$—OOCNH—$R^8$—NHCOO)$_q$—$R^7$—O— wherein $R^7$, $R^8$, and q are as defined above.

The softer segments may therefore be described by the more general formula (—O or —OCNH)—($R^a$—U—$R^b$—U)$_y$—$R^a$—(O— or NHCO—). In this formula, each $R^a$ and $R^b$ is independently a hydrocarbon backbone having a molecular weight of less than about 1000, wherein at least one is a hydrocarbon backbone of a noncrystallizing hydrocarbon derivative, and U signifies a urethane group. The "y" signifies the average number of repeating units, which is typically about 1–1000.

The harder segments may be described by the more general formula (—O or —OCNH)—($R^c$—U—$R^d$—U)$_z$—$R^c$—(O— or NHCO—). In this formula, each $R^c$ and $R^d$ is independently a hydrocarbon moiety having a molecular weight of less than about 1000, wherein at least one is crystallizing at ambient temperature, U signifies a urethane group. The "z" signifies the average number of repeating units, which is typically about 1–1000.

In the more general formula set forth above, the hydrocarbon moieties in the softer segment should not be construed to be limited to a particular or single hydrocarbon moiety, but may include one or more different hydrocarbon moieties. As discussed above, in some embodiments, a mix of short and medium chain hydrocarbon moieties is believed desirable. With regard to $R^c$ and $R^d$, the choice of separate designators for the $R^c$ and $R^d$ hydrocarbon moieties should not be considered to require that they are differing hydrocarbon moieties, but is intended only to reflect the fact that one of $R^c$ and $R^d$ is derived from a diisocyanate and the other is derived from a diol.

Any of the R or D groups defined in these soft and hard polyurethane segments can include the sacrificial moiety, particularly sulfur- and phosphorus-containing moieties. Preferably, however, the sacrificial moiety is incorporated into the polymers using diols, such as 2,2'-thiodiethanol, 3,6-dithia-1,8-octanediol, 1,4-dithiane-2,5-diol, 4,4'-thiodibutanol, and bis-hydroxypropyl phosphine (available from Cytec Industries, Inc., West Peterson, N.J.), for example.

The polymers described herein may be isocyanate, hydroxyl, and/or amino terminated depending on the stoichiometric amounts of monomers used. Slightly hydroxyl terminated polymers are preferred for long term stability of the mechanical properties and molecular weight of the polymer. It appears equally beneficial to "end cap" isocyanate terminated polymers with a monoalcohol to enhance stability.

The polymers described herein may be prepared using a one- or two-stage process. In a one-stage process, all the reactants are blended together and allowed to polymerize in a random fashion. The two-stage process comprises initially combining noncrystalline isocyanate with medium or medium and short chain diols or amines in a ratio of NCO:OH (or NCO:$NH_2$) of about 1:2 to 4:5, and more preferably of about 2:3. For certain of the polymers, the stoichiometric ratio of the medium chain to short chain diols and/or amines preferably is about 1:3 to 4:1. However, useful polymers may be produced using only medium chain or short chain diols and/or amines in the first stage. The combined reactants of the first stage are allowed to react until substantially no isocyanate functional groups remain to produce a hydroxyl or amine terminated prepolymer.

The second stage comprises the addition of short to medium chain diols and/or amines and short to medium chain diisocyanates to the adduct produced by the first stage. Preferably, the excess of diisocyanates in the second stage is about equal to the excess of diols and/or amines in the first stage to provide a generally balanced polymer. The total stoichiometric ratio of first stage to second stage reactants may be adjusted to obtain desired physical properties.

The polymers produced according to the examples outlined below have been found to demonstrate improved mechanical properties upon oxidation (at least upon initial oxidation). In particular, polyurethanes prepared from dimer diisocyanate, 2,2'-thiodiethanol, 1,4-cyclohexane dimethanol, 1,6-hexane duisocyanate have been tested and compared with the same formulation that had been exposed to oxidants. The exposed formulation showed an increase in strength over the nonexposed formulation (at least upon initial oxidation). That is, although the polymers are oxidized, their mechanical properties are enhanced. As a result, polyurethanes produced according to the present invention are believed to be particularly appropriate for use in implantable devices and are believed to be substantially superior to presently available polyurethane formulations.

An example of a medical device for which the polymers are particularly well suited is a medical electrical lead, such as a cardiac pacing lead, a neurostimulation lead, leads employing electrical transducers, etc. Examples of such leads are disclosed, for example, in U.S. Pat. No. 5,040,544 (Lessar et al.), U.S. Pat. No. 5,375,609 (Molacek et al.), U.S. Pat. No. 5,480,421 (Otten), and U.S. Pat. No. 5,238,006 (Markowitz). An example of a cardiac pacing lead is shown in FIG. 1. The pacing lead 10 includes a connector assembly at its proximal end, including a first conductive surface 12, a second conductive surface 14, and two insulative segments 16 and 18. Insulative segments 16 and 18 are each provided with a plurality of sealing rings 20. Extending from the connector assembly is an elongated lead body, including an outer insulative sheath 22, which is formed from the polymers described above. Within insulative sheath 22 is located an elongated conductor (not shown), such as a quadrifilar, multiconductor coil, which is described in U.S. Pat. No. 5,040,544 (Lessar et al.). Two of the conductors within the coil are coupled to conductive surface 12, and the other two are coupled to conductive surface 14. At the distal end of the lead are located a ring electrode 24, coupled to two of the conductors, and a tip electrode 26, coupled to the other two of the four conductors of the quadrifilar coil. Extending between ring electrode 24 and tip electrode 26 is an additional insulative sheath 28. Such medical electrical leads can be implanted into a vein or artery of a mammal and electrically connected to an implantable medical device.

The invention has been described with reference to various specific and preferred embodiments and will be further described by reference to the following detailed examples. It is understood, however, that there are many extensions, variations, and modification on the basic theme of the present invention beyond that shown in the examples and detailed description, which are within the spirit and scope of the present invention.

EXAMPLES

Test Methods

At least 8 replicates of each of 16 polyurethane film samples were cut into no less than 10 cm×2 cm rectangles. The unused films were stored under nitrogen in the dark. Screw capped jars were prepared with enough 12.5% hydrogen peroxide so that the eight 10 cm×2 cm samples would be completely covered. The 8 replicates for each of the 16 formulations were placed into a separate jar (16 jars total) and covered with a known volume of the peroxide solution. The 17th jar was set up as a control with no polyurethane samples but the same volume of peroxide solution. The 17 jars were placed in a 37° C. oven (in the dark) and the date and time were noted.

The samples were rinsed with water and dried under vacuum for 24 hours before testing. Samples of the 100% modified polymers were evaluated at two weeks, four weeks, five weeks, six weeks, and eight weeks. Each replicate was analyzed using FTIR analysis using attenuated total reflectance techniques (ATR), a Zinc Selenide (ZnSe) ATR crystal, and scanned at a 45° angle of incidence. The absorbance peak at 1030 $cm^{-1}$ was used to measure the oxidation of the thiol group (R—S—R) to the sulfoxy (R—SO—R'). This peak can be masked, however, in the spectra of certain polymer formulations. The absorbance peak at 1125 $cm^{-1}$ was used to measure the oxidation of the sulfoxy group to the sulfone (R—$SO_2$—R').

Tensile testing was performed using ASTM D1708 (microtensile). The microtensile dogbone shape was used to cut test samples from the films. An MTS Sintech Model 1/D tensile tester was used. Samples were gripped at 80 psi, using a gauge length of 0.876 inches. The crosshead speed was 5 inches/minute. The elastic modulus (Young's modulus) and the ultimate tensile strength were measured.

Dynamic Mechanical Analysis (DMA) was performed on a Perkin Elmer DMA-7e. The films were tested in tension. Samples of uniform rectangular shape were measured for thickness and width prior to mounting. A temperature scan was performed on samples in tension at 1 Hz from 150° C. to 130° C. at 4° C./minute using 120% tension control and 5 micrometer amplitude control. The elastic modulus (i.e., storage modulus or modulus of elasticity) was measured as a function of temperature. For thiodiethanol-derivatized samples oxidized over various times over 8 weeks, temperature scans were performed in compression at 1 Hz from −50° C. to 170° C. at 5° C./minute using 120% tension control.

Gel permeation chromatography (GPC) was performed using a Waters 150 CV with a Refractive Index detector. The samples were dissolved in dimethylacetamide (DMAC) and analyzed using a relative polystyrene calibration.

The conditions of the analyses were as follows: DMAC mobile phase; 0–8 ml/minute flow rate; HT4-HT3-HT2 column set; 70° C. column, sample, and detector temperatures.

Formulations of Antioxidant-Containing Polyurethanes

All reactions were performed in a nitrogen-purged drybox. All diols were dried prior to use by application of heat and vacuum. A polypropylene beaker was typically used as the reaction vessel and reactions were mixed by hand using a polyacetal stirring rod. 2,2'-Thiodiethanol (TDE), 1,4-butanediol (BDO), 1,4-cyclohexanedimethanol (CHDM), 1,6-diisocyanatohexane (HDI), and 4,4'-disocyanatodiphenyl methane (MDI) were purchased from Aldrich Chemical Company (Milwaukee, Wis.) and used as received. The diisocyanate derivative of dimer acid (DDI) was purchased from Henkel Corporation (Chicago, Ill.) and used as received. The diol derivative of dimer acid (DIMEROL) was purchased from Unichema International and used as received.

Control 1

The polyurethane (Formulation I) used as the standard of comparison for Examples 1–9 was formulated as follows: 27.04 g 1,4-cyclohexanedimethanol, 5.63 g BDO, and 118.37 g of the diisocyanate derivative of dimer acid were combined in a polypropylene beaker and stirred thoroughly until combined. The mixture was placed in a 50° C. oven and stirred every 15 minutes until the mixture was homogeneous and no IR bands due to NCO appeared. BDO (9.01 g) was stirred in followed quickly by 25.23 g HDI. The mixture was stirred until set and cured in a 100° C. oven for 24 hours.

Example 1

The polyurethane of Formulation I was modified by substituting one mole percent of the 1,4-butanediol with 2,2'-thiodiethanol in both the hard and soft segment as follows: 98.65 g 1,4-butanediol and 1.35 g 2,2'-thiodiethanol were stirred together until combined. In a separate polypropylene beaker, 27.04 g CHDM, 5;65 g of the BDO/TDE mixture, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. The BDO/TDE mixture (9.04 g) was stirred into the mixture, quickly followed by 25.23 g 1.6-diisocyanatohexane. The resultant mixture was stirred until set and cured in a 100° C. oven for 24 hours to produce a polymer with 0.028 weight percent sulfur.

Example 2

The polyurethane of Formulation I was modified by substituting five mole percent of the 1,4-butanediol with 2,2'-thiodiethanol in both the hard and soft segment as follows: 93.34 g 1,4-butanediol (BDO) and 6.66 g 2,2'-thiodiethanol were stirred together until combined. In a separate polypropylene beaker, 27.04 g 1,4-cyclohexanedimethanol (CHDM), 5.73 g of the BDO/TDE mixture, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. The BDO/TDE mixture (9.17 g) was stirred into the mixture, quickly followed by 25.23 g 1,6-diisocyanatohexane. The resultant mixture was stirred until set and cured in a 100° C. oven for 24 hours to produce a polymer with 0.140 weight percent sulfur.

Example 3

The polyurethane of Formulation I was modified by substituting ten mole percent of the 1,4-butanediol with by 2,2'-thiodiethanol in both the hard and soft segment as follows: 86.91 g 1,4-butanediol and 13.09 g 2,2'-thiodiethanol were stirred together until combined. In a separate polypropylene beaker, 27.04 g CHDM, 5.83 g of the BDO/TDE mixture, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. The BDO/TDE mixture (9.33 g) was stirred into the mixture, quickly followed by 25.23 g 1,6-diisocyanatohexane. The resultant mixture was stirred until set and cured in a 100° C. oven for 24 hours to produce a polymer with 0.280 weight percent sulfur.

Example 4

The polyurethane of Formulation I was modified by substituting 25 mole percent of the 1,4-butanediol with 2,2'-thiodiethanol in both the hard and soft segment as follows: 68.87 g 1,4-butanediol and 31.13 g 2,2'-thiodiethanol were stirred together until combined. In a separate polypropylene beaker, 27.04 g CHDM, 6.13 g of the BDO/TDE mixture, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. The BDO/TDE mixture (9.81 g) was stirred into the mixture, quickly followed by 25.23 g 1,6-diisocyanatohexane. The resultant mixture was stirred until set and cured in a 100° C. oven for 24 hours to produce a polymer with 0.698 weight percent sulfur.

Example 5

The polyurethane of Formulation I was modified by substituting 50 mole percent of the 1,4-butanediol with 2,2'-thiodiethanol in both the hard and soft segment as follows: 42.44 g 1,4-butanediol and 57.56 g 2,2'-thiodiethanol were stirred together until combined. In a separate polypropylene beaker, 27.04 g CHDM, 6.63 g of the BDO/TDE mixture, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. The BDO/TDE mixture (10.62 g) was stirred into the mixture, quickly followed by 25.23 g 1,6-diisocyanatohexane. The resultant mixture was stirred until set and cured in a 100° C. oven for 24 hours to produce a polymer with 1.386 weight percent sulfur.

Example 6

The polyurethane of Formulation I was modified by substituting 75 mole percent of the 1,4-butanediol with 2,2'-thiodiethanol in both the hard and soft segment as follows: 19.73 g 1,4-butanediol and 80.27 g 2,2'-thiodiethanol were stirred together until combined. In a separate polypropylene beaker, 27.04 g CHDM, 7.14 g of the BDO/TDE mixture, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. The BDO/TDE mixture (11.42 g) was stirred into the mixture, quickly followed by 25.23 g 1,6-diisocyanatohexane. The resultant mixture was stirred until set and cured in a 100° C. oven for 24 hours to produce a polymer with 2.065 weight percent sulfur.

Example 7

The polyurethane of Formulation I was modified by substituting all the 1,4-butanediol with 2,2'-thiodiethanol in both the hard and soft segment as follows: in a polypropylene beaker, 27.04 g CHDM, 7.64 g TDE, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. An additional 12.22 g TDE were stirred into the mixture, quickly followed by 25.23 g 1,6-diisocyanatohexane. The mixture was stirred until set and cured in a 100° C. oven for 24 hours to produce a polymer with 2.734 weight percent sulfur.

Example 8

The polyurethane of Formulation I was modified by substituting BDO with 3,6-dithia-1,8-octanediol (available from Aldrich Chemical Company, Madison, Wis.) as follows in a polypropylene beaker, 27.04 g CHDM, 11.40 g 3,6-dithia-1,8-octanediol, and 118.37 g of the diisocyanate derivative of dimer acid were combined and stirred thoroughly. The mixture was placed in a 50° C. oven and stirred every 15 minutes until the mixture was homogeneous and no IR bands due to NCO appeared. An additional 18.23 g 3,6-dithia-1,8-octanediol were stirred into the mixture, quickly followed by 25.23 g HDI. The mixture was stirred until set and cured in a 100° C. oven for 24 hours.

Example 9

The polyurethane of Formulation I was modified by substituting BDO with 4,4'-thiodibutanol as follows: in a polypropylene beaker, 27.04 g CHDM, 11.15 g 4,4'-thiodibutanol (synthesized by reacting two moles of 4-chloro-1-butanol with one mole of sodium sulfide under phase transfer conditions, and then the product was distilled to give the pure 4,4'-thiodibutanol), and 118.37 g of the diisocyanate derivative of dimer acid were combined and stirred thoroughly. The mixture was placed in a 50° C. oven and stirred every 15 minutes until the. mixture was homogeneous and no IR bands due to NCO appeared. An additional is 17.83 g 4,4'-thiodibutanol were stirred into the mixture, quickly followed by 25.23 g HDI. The mixture was stirred until set and cured in a 100° C. oven for 24 hours.

Control 2

The polyurethane (Formulation II) used as the standard of comparison for Examples 10–16 was formulated as follows: 11.36 g DIMEROL, 3.60 g BDO, and 23.67 g of DDI were combined in a polypropylene beaker and stirred thoroughly until combined. The mixture was placed in a 50° C. oven and stirred every 15 minutes until the mixture was homogeneous and no IR bands due to NCO appeared. BDO (1.80 g) was stirred in followed quickly by 25.10 g MDI and 34.08 g DIMEROL. The mixture was stirred until set and cured in a 100° C. oven for 24 hours.

Example 10

The polyurethane of Formulation II was modified by substituting one mole percent of the 1,4-butanediol with 2,2'-thiodiethanol in both the hard and soft segment as follows: 98.65 g BDO and 1.35 g TDE were stirred together until combined. In a separate polypropylene beaker, 11.36 g DIMEROL, 3.62 g of the BDO/TDE mixture, and 23.67 g of DDI were combined and stirred thoroughly. The mixture was placed in a 50° C. oven and stirred every 15 minutes until the mixture was homogeneous and no IR bands due to NCO appeared. The BDO/TDE mixture (1.81 g) was stirred into the mixture, quickly followed by 25.10 g MDI and 34.08 g DIMEROL. The resultant mixture was stirred until set and cured in a 100° C. oven for 24 hours to produce a polymer with 0.019 weight percent sulfur.

Example 11

The polyurethane of Formulation II was modified by substituting five mole percent of the 1,4-butanediol with 2,2'-thiodiethanol in both the hard and soft segment as follows: 93.34 g BDO and 6.66 g TDE were stirred together until combined. In a separate polypropylene beaker, 11.36 g DIMEROL, 3.67 g of the BDO/TDE mixture, and 23.67 g of DDI were combined and stirred thoroughly. The mixture was placed in a 50° C. oven and stirred every 15 minutes until the mixture was homogeneous and no IR bands due to NCO appeared. The BDO/TDE mixture (1.83 g) was stirred into the mixture, quickly followed by 25.10 g MDI and 34.08 g DIMEROL. The resultant mixture was stirred until set and cured in a 100° C. oven for 24 hours to produce a polymer with 0.096 weight percent sulfur.

Example 12

The polyurethane of Formulation II was modified by substituting ten mole percent of the 1,4-butanediol with 2,2'-thiodiethanol in both the hard and soft segment as follows: 86.91 g BDO and 13.09 g TDE were stirred together until combined. In a separate polypropylene beaker, 11.36 g DIMEROL, 3.74 g of the BDO/TDE mixture, and 23.67 g of DDI were combined and stirred thoroughly. The mixture was placed in a 50° C. oven and stirred every 15 minutes until the mixture was homogeneous and no IR bands due to NCO appeared. The BDO/TDE mixture (1.86 g) was stirred into the mixture, quickly followed by 25.10 g MDI and 34.08 g DIMEROL. The resultant mixture was stirred until set and cured in a 100° C. oven for 24 hours to produce a polymer with 0.193 weight percent sulfur.

Example 13

The polyurethane of Formulation II was modified by substituting 25 mole percent of the 1,4-butanediol with 2,2'-thiodiethanol in both the hard and soft segment as follows: 68.87 g BDO and 31.13 g TDE were stirred together until combined. In a separate polypropylene beaker, 11.36 g DIMEROL, 3.93 g of the BDO/TDE mixture, and 23.67 g of DDI were combined and stirred thoroughly. The mixture was placed in a 50° C. oven and stirred every 15 minutes until the mixture was homogeneous and no IR bands due to NCO appeared. The BDO/TDE mixture (1.96 g) was stirred into the mixture, quickly followed by 25.10 g MDI and 34.08 g DIMEROL. The resultant mixture was stirred until set and cured in a 100° C. oven for 24 hours to produce a polymer with 0.480 weight percent sulfur.

Example 14

The polyurethane of Formulation II was modified by substituting 50 mole percent of the 1,4-butanediol with 2,2'-thiodiethanol in both the hard and soft segment as follows: 42.44 g BDO and 57.56 g TDE were stirred together until combined. In a separate polypropylene beaker, 11.36g DIMEROL, 4.25 g of the BDO/TDE mixture, and 23.67 g of DDI were combined and stirred thoroughly. The mixture was placed in a 50° C. oven and stirred every 15 minutes until the mixture was homogeneous and no IR bands due to NCO appeared. The BDO/TDE mixture (2.12 g) was stirred into the mixture, quickly followed by 25.10 g MDI and 34.08 g DIMEROL. The resultant mixture was stirred until set and cured in a 100° C. oven for 24 hours to produce a polymer with 1.427 weight percent sulfur.

Example 15

The polyurethane of Formulation II was modified by substituting 75 mole percent of the 1,4-butanediol with 2,2'-thiodiethanol in both the hard and soft segment as follows: 19.73 g BDO and 80.27 g TDE were stirred together until combined. In a separate polypropylene beaker, 11.36 g DIMEROL, 4.57 g of the BDO/TDE mixture, and 23.67 g of DDI were combined and stirred thoroughly. The mixture was placed in a 50° C. oven and stirred every 15 minutes until the mixture was homogeneous and no IR bands due to NCO appeared. The BDO/TDE mixture (2.28 g) was stirred into the mixture, quickly followed by 25.10 g MDI and 34.08 g DIMEROL. The resultant mixture was stirred until set and cured in a 100° C. oven for 24 hours to produce a polymer with 1.427 weight percent sulfur.

Example 16

The polyurethane of Formulation II was modified by substituting all the 1,4-butanediol with 2.2'-thiodiethanol in both the hard and soft segment as follows: in a polypropylene beaker, 11.36 g DIMEROL, 4.89 g TDE, and 23.67 g of DDI were combined and stirred thoroughly. The mixture was placed in a 50° C. oven and stirred every 15 minutes until the mixture was homogeneous and no IR bands due to NCO appeared. An additional 2.44 g TDE were stirred into the mixture, quickly followed by 25.10 g MDI and 34.08 g DIMEROL. The mixture was stirred until set and cured in a 100° C. oven for 24 hours to produce a polymer with 1.893 weight percent sulfur.

After cure, the polyurethanes were processed by freezing in liquid nitrogen, breaking into pieces, and drying in a vacuum oven at 60° C. for 48 hours. The polymers were pressed at 165° C. to give films 0.020–0.025 inches thick. These films were annealed in a 60° C. oven for 48 hours, and these annealed films were the source from which samples for the testing of tensile properties were cut.

Results

In the first study, Formulation II was modified with either 1% or 100% TDE and Formulation I was modified with 1% TDE. Samples were oxidized for 8 weeks. Tensile testing compared the oxidized samples to the corresponding unoxidized controls (Table 1; n≧5). The Formulation II with 100% TDE sample increased in both ultimate tensile strength (became stronger) and Young's modulus (became harder) after 8 weeks of oxidation. This is an advantage, since oxidation typically weakens polymers. There was little difference in the test values before and after oxidation for both Formulations I and II containing only 1% TDE.

TABLE 1

Tensile Testing of Oxidized and Unoxidized Formulations Containing TDE.

| Formulation | Oxidized | tensile strength, psi | Young's modulus, psi |
|---|---|---|---|
| II with 100% TDE | Y | 3,530 ± 320 | 14,530 ± 1,620 |
|  | N | 2,840 ± 300 | 9,470 ± 990 |
| II with 1% TDE | Y | 4,270 ± 260 | 3,550 ± 550 |
|  | N | 4,330 ± 380 | 3,900 ± 250 |
| I with 1% TDE | Y | 4,100 ± 390 | 6,340 ± 250 |
|  | N | 3,890 ± 300 | 6,200 ± 380 |

Figure 4:
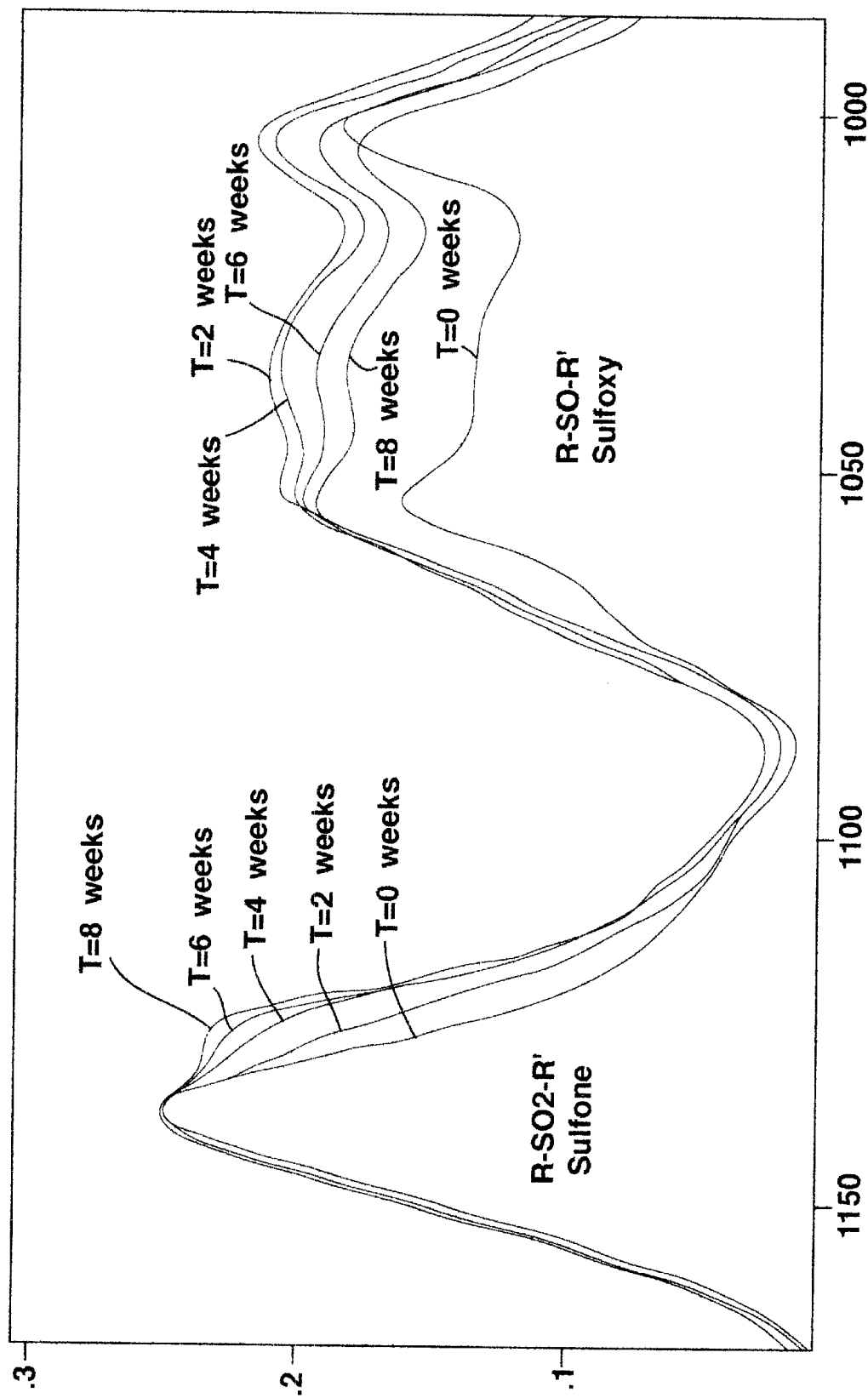
FIG. 4 is an infrared spectrum of the polymeric biomaterial of FIG. 3 of the present invention with time in an oxidizing environment.

The FTIR analysis of the polymer film during oxidation was performed during the second study to monitor the oxidation process. Formulation I was used to monitor the formation of sulfoxy groups (R—SO—R'). This can be seen in the spectra at 1030 cm$^{-1}$ (FIG. 4). The subsequent oxidation of the sulfoxy group to the sulfone was also observed in the spectra of Formulation 1. The shoulder peak at 1125cm$^{-1}$ became more pronounced as the oxidation time increased but the sulfoxy peak began to lessen at around the four to five week time period. This suggests that the conversion of sulfoxy to sulfone was occurring. The region in the spectra which is indicative of the sulfoxy group is masked but the region indicative of the sulfone is clear. The sulfone peak became more pronounced as oxidation progressed. There appeared to be no other noticeable oxidation/degradation of the polymer based on the infrared data.

Figure 2:
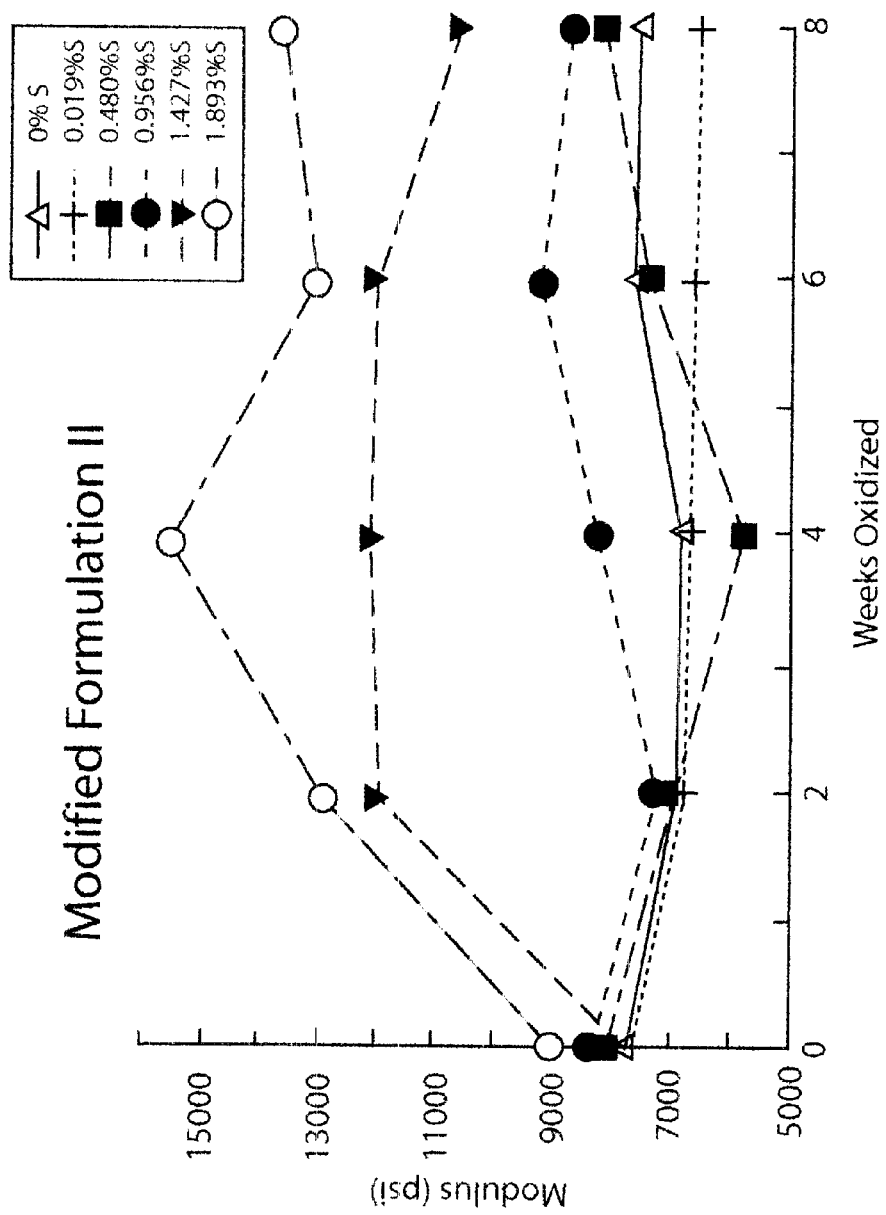
FIG. 2 is a graph of the modulus of elasticity of a polymeric biomaterial of the present invention with time in an oxidizing environment.

In a subsequent study, Formulations I and II were prepared with either 0, 1, 5, 10, 25, 50, 75, or 100% TDE to help determine the useful range in TDE content. Film samples were oxidized and tested at 0, 2, 4, 6, and 8 weeks. The mechanical properties were measured by DMA (n=1). FIG. 2 and Table 2 show how the DMA storage modulus of the TDE-modified Formulation II varied with oxidation time. Compared to the modulus values before oxidation, only the formulations containing 75% or 100% TDE increased significantly in modulus with oxidation time, indicating an increase in hardness.

TABLE 2

Effect of Oxidation on DMA Modulus of Elasticity for TDE-Modified Formulation II.

| | DMA Modulus of Elasticity (psi, at 23° C.) | | | | | |
|---|---|---|---|---|---|---|
| Oxidation (weeks) | 0% TDE | 1% TDE | 25% TDE | 50% TDE | 75% TDE | 100% TDE |
| 0 | 7810 | 7700 | 8070 | 8380 | 7720 | 8910 |
| 2 | 6970 | 6710 | 6900 | 7160 | 12000 | 12860 |
| 4 | 6700 | 6600 | 5740 | 8200 | 12090 | 15520 |
| 6 | 7510 | 6510 | 7330 | 9160 | 11960 | 12960 |
| 8 | 7470 | 6430 | 8050 | 8650 | 10550 | 13580 |

Figure 3:
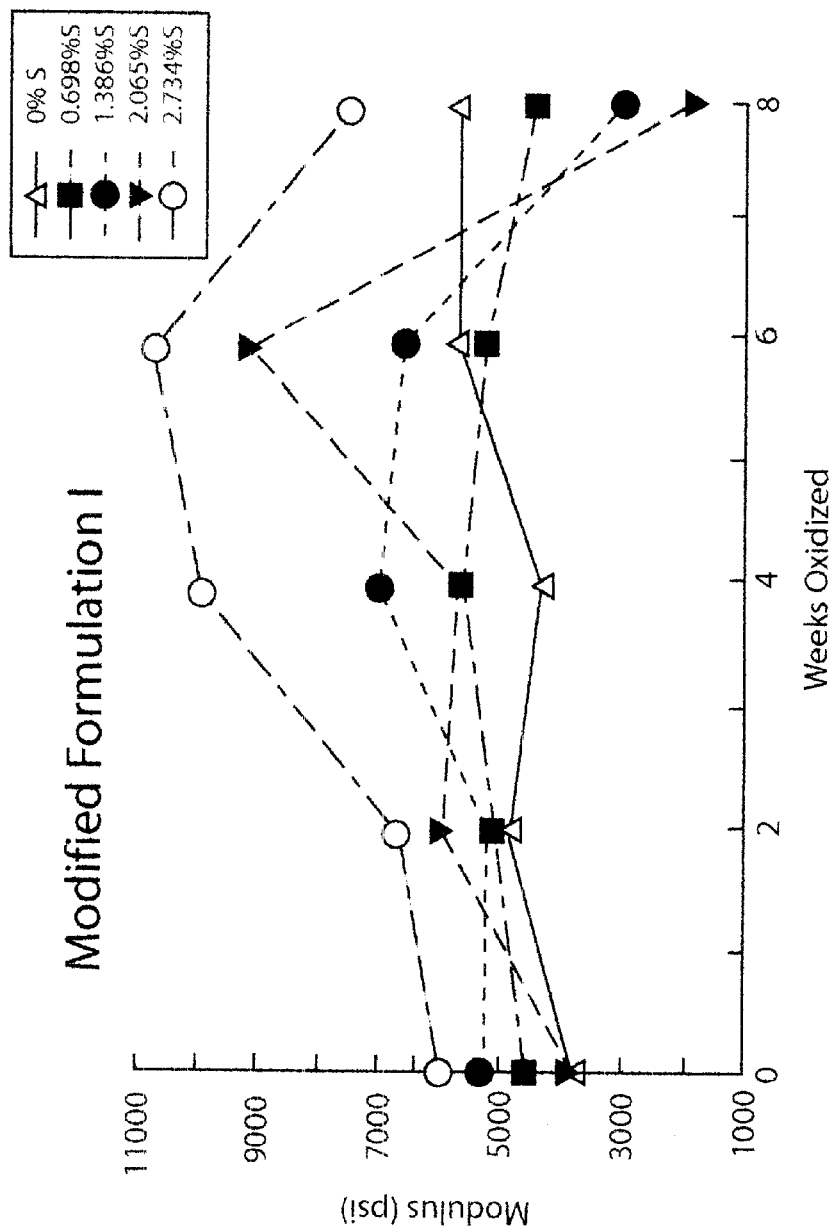
FIG. 3 is a graph of the modulus of elasticity of an alternative polymeric biomaterial of the present invention with time in an oxidizing environment.

FIG. 3 and Table 3 show how the DMA storage modulus of the TDE-modified Formulation I varied with oxidation time. Compared to the modulus values before oxidation, the formulation containing 100% TDE increased significantly in modulus and remained above its initial values with continued oxidation time. The formulation containing 75% TDE increased significantly above its initial value by 6 weeks, but dropped to below the initial modulus value at 8 weeks. This is believed to be due to continued oxidation and perhaps the beginning stages of degradation.

TABLE 3

Effect of Oxidation on DMA Storage Modulus for TDE-Modified Formulation I.

| Oxidation | DMA Storage Modulus (psi, at 23° C.) | | | | |
|---|---|---|---|---|---|
| (weeks) | 0% TDE | 25% TDE | 50% TDE | 75% TDE | 100% TDE |
| 0 | 3790 | 4550 | 5230 | 3810 | 5980 |
| 2 | 4840 | 5030 | 5130 | 5920 | 6660 |
| 4 | 4240 | 5530 | 6880 | 5620 | 9800 |
| 6 | 5560 | 5100 | 6440 | 8950 | 10520 |
| 8 | 5540 | 4310 | 2820 | 1680 | 7310 |

DMA temperature scans of the 100% TDE-modified Formulation II before and after 8 week oxidation were taken. The glass transition temperature of the formulation was affected by the oxidation, as evidenced in the shift in the peak in tan δ to higher temperatures. The glass transition of the 100% Formulation II was converted into two transitions after oxidation, the peaks shifting about 10° C. and 30° C. as compared to the transition before oxidation (Table 4). The glass transition was one broad peak before oxidation but became more sharp, splitting into two more well defined peaks after the 8 week oxidation. The glass transition is characteristic of the primary structure of the polymer, and it is actually reflected by the chemical structure of the polymerized monomers. These data support the chemical changing of the primary structure of the polymer. The sulfide group in the unoxidized TDE monomer units was thought to have oxidized to a sulfoxide and/or a sulfone. Since two new tan δ peaks occurred after oxidation, they may have been due to oxidation of the TDE to TDE-sulfoxide and TDE-sulfone. It makes sense that the glass transition would increase upon oxidation since a sulfoxide or a sulfone group are both more bulky than a sulfide group. A shift of the glass transition to a higher temperature will also result in a shift of the modulus—temperature curve. This used the modulus to be greater at ambient temperature after oxidation. This would be beneficial because it would lead to harder, and possibly stronger, materials after oxidation.

TABLE 4

DMA Glass Transition Temperatures for Unoxidized and Oxidized 100% TDE-Modified Formulation II.

| Sample | tan δ peak (° C.) | tan δ onset (° C.) |
|---|---|---|
| Not oxidized | 32 | −5 |
| Oxidized 8 weeks | 41, 61 | 24, 55 |

The GPC analysis of the polymers was carried out and suggested a change in the molecular weight distribution of the oxidized polymers. The samples contained a primary peak indicative of the polymer's distribution. This remained fairly stable for similar samples as the oxidation time increased. That is, the peak molecular weight of the primary peak was fairly constant going from 0 weeks (control) to the 8 week time of polymer modified with like amounts of TDE. A difference in the relative ratio of a higher molecular weight component as compared to the primary peak as a function of oxidation was observed. The higher molecular weight peak increased in intensity relative to the primary peak. This may suggest that the thiol modification and subsequent oxidation may increase the overall molecular weight distribution. The polymers also do not appear to have undergone noticeable degradation based on the lack of lower molecular weight species in the chromatogram and the stability of the primary GPC peak.

The complete disclosure of all patents, patent documents, and publications cited herein are incorporated by reference, as if individually incorporated. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of making a medical device comprising a biomaterial; the method comprising:

(a) combining at least one isocyanate-containing compound with at least one diol- or diamine-containing compound to form the biomaterial comprising at least one urea group and at least one sacrificial moiety that preferentially oxidizes relative to all other moieties in the polymer; and (b) forming a medical device with the biomaterial.

2. The method of claim 1 wherein the biomaterial comprises at least one sulfur-containing moiety, at least one phosphorus-containing moiety, or combinations thereof.

3. The method of claim 1 wherein the medical device comprises an electrical lead.

4. The method of claim 1 wherein the biomaterial comprises a segmented polyurethane.

5. The method of claim 1 wherein the sacrificial moieties comprise at least about 1.2 weight percent of an oxidizable element, based on the total weight of the polymer.

* * * * *